(12) United States Patent
Schönauer

(10) Patent No.: US 6,432,168 B2
(45) Date of Patent: Aug. 13, 2002

(54) MEASURING ARRANGEMENT AND METHOD FOR MONITORING THE OPERABILITY OF A SOOT FILTER

(75) Inventor: Ulrich Schönauer, Eggenstein (DE)

(73) Assignee: EPIQ Sensor-Nite N.V., Leuven (BE)

( * ) Notice: Subject to any disclaimer, the term of this patent is extended or adjusted under 35 U.S.C. 154(b) by 0 days.

(21) Appl. No.: 09/732,544

(22) Filed: Dec. 8, 2000

(30) Foreign Application Priority Data

Dec. 10, 1999 (DE) .......................................... 199 59 870

(51) Int. Cl.⁷ ........................... F01N 3/021; G01N 25/32
(52) U.S. Cl. ........................... 95/18; 95/283; 55/282.3; 55/283; 55/DIG. 10; 55/DIG. 30; 60/274
(58) Field of Search ............................ 95/14, 18, 278, 95/283; 55/282.3, 283, 309.1, 385.3, 428.1, 466, DIG. 10, DIG. 30; 60/274, 303

(56) References Cited

U.S. PATENT DOCUMENTS

| | | | |
|---|---|---|---|
| 4,372,111 A | * 2/1983 | Virk et al. | 60/274 |
| 4,404,795 A | 9/1983 | Oishi et al. | 55/466 |
| 4,656,832 A | 4/1987 | Yukihisa et al. | |
| 5,489,319 A | * 2/1996 | Tokuda et al. | 55/DIG. 30 |
| 5,531,068 A | * 7/1996 | Kass et al. | 60/274 |
| 5,651,250 A | * 7/1997 | Kawamura | 60/303 |
| 6,090,187 A | * 7/2000 | Kumagai | 95/278 |

FOREIGN PATENT DOCUMENTS

| | | |
|---|---|---|
| DE | 38 03 100 A1 | 8/1989 |
| DE | 39 29 303 A1 | 3/1991 |
| DE | 39 35 149 A1 | 5/1991 |
| DE | 37 43 559 C2 | 11/1991 |
| DE | 40 20 385 A1 | 1/1992 |
| DE | 197 48 561 A1 | 5/1999 |

* cited by examiner

Primary Examiner—David A. Simmons
Assistant Examiner—Frank M. Lawrence
(74) Attorney, Agent, or Firm—Akin, Gump, Strauss, Hauer & Feld, L.L.P.

(57) ABSTRACT

A measuring arrangement is provided with a soot filter for use in flowing, soot particle-bearing gases, as well as a method for monitoring the operability of a soot filter arranged in an exhaust gas conduit, wherein at least one component stream of an exhaust gas stream flows through at least one molded element which is open-pored at least in the flow direction, and wherein the temperature of the molded element is measured with at least one temperature probe. In the measuring arrangement the soot filter is allocated at least one soot sensor, which has at least one molded element which is openpored at least in the flow direction, at least one electric heating element, and at least one temperature probe. The measuring arrangement and method make possible a monitoring of the operability of a soot filter in a reliable and direct manner.

19 Claims, 7 Drawing Sheets

MEASURING ARRANGEMENT AND METHOD FOR MONITORING THE OPERABILITY OF A SOOT FILTER

BACKGROUND OF THE INVENTION

The invention relates to a measuring arrangement with a soot filter for use in flowing, soot particle-bearing gases and its use, as well as a method for monitoring the operability of a soot filter arranged in an exhaust gas conduit, wherein at least one component stream of an exhaust gas stream flows through at least one molded element, which is open-pored at least in the flow direction, and wherein the temperature of the molded element is measured with at least one temperature probe.

Soot filters are chiefly used for filtering of soot particle-containing exhaust gases from internal combustion engines, preferably from diesel motors. The soot filter becomes contaminated with soot particles in the course of time, and must then either be exchanged or cleaned. The cleaning is here the more economical method and can take place continuously or at a certain point in time. The time for a cleaning can be selected at fixed time intervals, or as a function of the loading of the soot filter.

U.S. Pat. No. 4,404,795 describes a method and a device for reducing the particle output in the exhaust gas of a diesel motor with the aid of a filter. With a rising number of soot particles in the soot filter, the free filter cross section drops, and the exhaust gas pressure upstream of the filter rises. The measurable exhaust gas pressure upstream of the filter is used to establish the time when the filter should be cleaned. Once the maximum allowable soot particle concentration in the soot filter is reached, then it is determined by a temperature probe when the filter temperature reaches the temperature which guarantees burning off the soot particles without an additionally applied quantity of heat. When this temperature is reached, the filter at the exhaust gas inlet is additionally heated to the combustion temperature of the soot particles, and, while adding secondary air to promote combustion, the burn off is started, and the filter is cleaned. Determining the point in time for cleaning the soot filter by a pressure measurement is an indirect measuring procedure and relatively subject to disturbance. Thus, a measured pressure increase, which is not to be attributed to a loading of the soot filter with soot, undeniably leads to a misinterpretation of the condition of the soot filter and to the conducting of an unnecessary cleaning. A cleaning of the filter by combustion of the soot should, however, only be conducted as often as is absolutely necessary, since it can lead to a defect or breakdown of the soot filter by overheating. Such a failure cannot, in turn, be recognized by this system itself.

There arises the problem of creating a measuring arrangement and a method with which a monitoring of the operability of the soot filter is made possible in a reliable and direct manner.

SUMMARY OF THE INVENTION

This problem is solved for the measuring arrangement in that the soot filter is allocated at least one soot sensor, which has at least one molded element, which is open-pored at least in the flow direction, at least one electrical heating element, and at least one temperature probe. The soot sensor makes possible a direct determination of the amount of soot on the soot filter.

The molded element can, for example, be subjected to through flow by a complete gas stream, which has soot particles, or instead only be subjected to through flow by a portion of the gas stream. The molded element should not take up 100% of the soot from the gas, thus not replace a soot filter. It is sensible in any given case for only a fraction of the soot to be taken up by the molded element subjected to through flow and, so to speak, for a representative portion of soot particles to be removed from the exhaust gas.

With respect to the large number of configuration possibilities of the sensor geometry of the soot sensor, care should be taken that conductive compounds as, for example, catalytically active material or the soot itself, do not lead to signal disturbances or short circuits, which can endanger a trouble free operation of the heating element as well as of the temperature probe. Possibly the use of one or more electrically-insulating, soot-impermeable layers between heating element and molded element or between temperature probe and molded element can be necessary for this.

The soot sensor can here be arranged upstream of the soot filter, in an exhaust gas bypass to the soot filter, or downstream of the soot filter. An arrangement in the soot filter is theoretically also possible, but an unintentional ignition of soot particles on the soot filter by the soot sensor must be ruled out. It is advantageous, however, if a first soot sensor is arranged upstream and a second soot sensor is arranged downstream of the soot filter.

By a molded element which is open-pored at least in the flow direction is quite generally to be understood an element with an open porosity or penetrating openings or holes in the flow direction, which can be present as ordered or unordered. Here, it can be a matter of a simple perforated sheet, a tube, a packet of fibers or wool, a porous ceramic, a porous glass, a porous thin layer, or the like. But even a very rough surface can be used as a molded element, which is open-pored in the flow direction. It is advantageous if the molded element is similar to the filter unit of the soot filter. Well suited, for example, is a ceramic molded element, which is open-pored at least in the flow direction, with a honeycomb construction, as typically used for catalytic converters in motor vehicles, as well as a foam ceramic. It is furthermore advantageous if the molded element is at least partially covered with a catalytically active material, for example with platinum. The ignition temperature of the soot is thereby reduced, and the energy requirement for the electrical heating element is diminished. Such a coating with catalytically active material is, for example, also typical in motor vehicle catalytic converters.

The electrical heating element and the temperature probe can be arranged directly on or in the molded element. The electrical heating element, the temperature probe and the molded element can also, however, be arranged on a carrier. In this connection, it is only important that the electrical heating element and the temperature probe be connected thermally conducting with the molded element.

The use of the measuring arrangement according to the invention in the exhaust gas conduit of a motor vehicle to test the operability of a soot filter especially suggests itself, since the soot sensor can be constructed with small dimensions and with low weight. But a use in other combustion facilities, in which exhaust gases with soot particles are generated, is also appropriate.

The problem is solved for the method in that a portion of the soot particles remains adhered on the molded element, and in that the molded element is heated to the ignition temperature of the soot by an electric heating element in defined time intervals, and in that a development of heat occurring with the combustion of soot particles is used as a direct measure for the operability of the soot filter. The molded element can, for example, be flowed through by the entire exhaust gas or instead be flowed through only by a portion of the exhaust gas. The molded element should not, however, replace a soot filter. It is sensible that, in any given case, only a fraction of the soot is filtered from the exhaust gas by the flowed-through molded element and, so to speak, a representative sample of soot particles is withdrawn from the exhaust gas.

Here, the time intervals, in which the molded element is heated with the electric heating element, can be selected as fixed. But variable time intervals, which can be selected on the basis of an evaluation of operating data, can also be appropriate. For a soot filter in the exhaust gas conduit of a diesel motor, this could mean, for example, that the heating of the molded element is started after a predetermined number of cold starts or as a function of the diesel fuel consumed. By operating data are accordingly to be understood generally information which relates to the generation of the exhaust gas and which can be set in some relationship with a development of soot in the exhaust gas.

First, it is possible that, after reaching the ignition temperature of the soot on the molded element, the electric heating element be operated at a constant heat output, that the development of heat arising from the combustion of the soot particles be measured with the temperature probe, that the temperature rise be evaluated as a direct measure for the combusted amount of soot particles on the molded element, and that the operability of the soot filter be determined therefrom. An intelligent control unit is necessary for this, which can convert the temperature rise into an amount of soot by a predetermined calculation routine. The amount of soot, which burns on the molded element, is proportional to the amount of soot, which has flowed by since the last heating of the molded element.

Second, after reaching the ignition temperature of the soot on the molded element, the temperature of the molded element can be held substantially isothermal by withdrawing the heat output of the heating element, and the decrease of the heat output can be evaluated as a direct measure for the combusted amount of soot particles, and the operability of the soot filter can be determined therefrom. Here as well, an intelligent control unit is necessary.

If a molded element is arranged in the flow direction upstream of the soot filter, then after reaching the ignition temperature of the soot, when a development of heat on the molded element occurs, the loading of the soot filter with soot particles can be determined.

After evaluating the temperature increase or the change in heat output and conversion into an amount of soot combusted on the molded element upstream of the soot filter, the loading of the soot filter itself is inferred. For this purpose, a correlation formula must be stored in the intelligent control unit, which contains the relationship between deposits on the molded element and the loading of the soot filter. If an amount of soot on the molded element is computed, which lies above an allowable, predetermined threshold value for the loading of the soot filter, then a cleaning of the soot filter is started by the control unit. If, however, a cleaning function is not planned for a soot filter, then upon reaching or exceeding the threshold value a notification, for example with a warning light or an acoustic signal, is emitted that the soot filter must be changed.

If, however, an amount of soot on the molded element is computed, which lies below an allowable, predetermined threshold value for the loading of the soot filter, then no cleaning of the soot filter or emission of a notification is started by the control unit, but instead the value calculated for the amount of soot is stored. A subsequently started, second determination of the amount of soot on the molded element, repeated at a certain interval from this first determination of the amount of soot on the molded element, must now be processed in connection with the first determination or the value stored for this purpose. The amount of soot calculated from of the second determination must be added to the stored value by the control unit, since in this case only the sum of both values in the correlation formula will provide the correct value for the loading of the soot filter. If the threshold value has still not been exceeded after the second determination, then the sum of the two determinations must be stored and used further for subsequent calculations in accordance with the formula above.

If a molded element is arranged in the flow direction downstream of the soot filter, a leak in the soot filter can be detected after reaching the ignition temperature of the soot upon occurrence of a development of heat, and a warning signal can be emitted which indicates the defect in the soot filter, if the development of heat exceeds a predetermined threshold value. Such leaks occur, for example, after a failure of the soot filter owing to breakage. After evaluation of the temperature increase or the change in heat output and conversion into a combusted amount of soot on the molded element downstream of the soot filter, the computed value is compared with a stored threshold value, which usually results from legally specified threshold values. If an amount of soot on the molded element is calculated, which indicates an insufficient filter action of the soot filter because of exceeding an allowable, predetermined threshold value, then a warning signal is emitted that a defect in the soot filter exists and that this must be changed.

If a first molded element is arranged in the flow direction upstream of the soot filter and a second molded element is arranged in the *flow direction downstream of the soot filter, then, after reaching the ignition temperature of the soot upon occurrence of a development of heat on the first molded element, the loading of the soot filter with soot particles can be ascertained, and after reaching the ignition temperature upon occurrence of a development of heat on the second molded element, a leak of the soot filter can be determined and a warning signal can be emitted, which indicates the defect in the soot filter, if the heat development exceeds a predetermined threshold value.

If two or more soot sensors are used, then the evaluation of the respective sensor signals need not take place in the same way at each of the soot sensors, but instead different evaluation methods can be used.

It is also possible to arrange one molded element in an exhaust gas bypass to the soot filter, where after reaching the ignition temperature of the soot upon occurrence of a development of heat on the molded element, the loading of the soot filter with soot particles can be ascertained. The evaluation here takes place as with an arrangement of the molded element upstream of the soot filter.

The following seven figures should provide an exemplary, detailed explanation of the measuring arrangement of the invention and the process. It should be expressly added that not only a planar construction of the soot sensor is possible, as it is shown here. The arrangement of the molded element on a rod or a tube or the use of a massive, self-supporting molded element is also possible.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
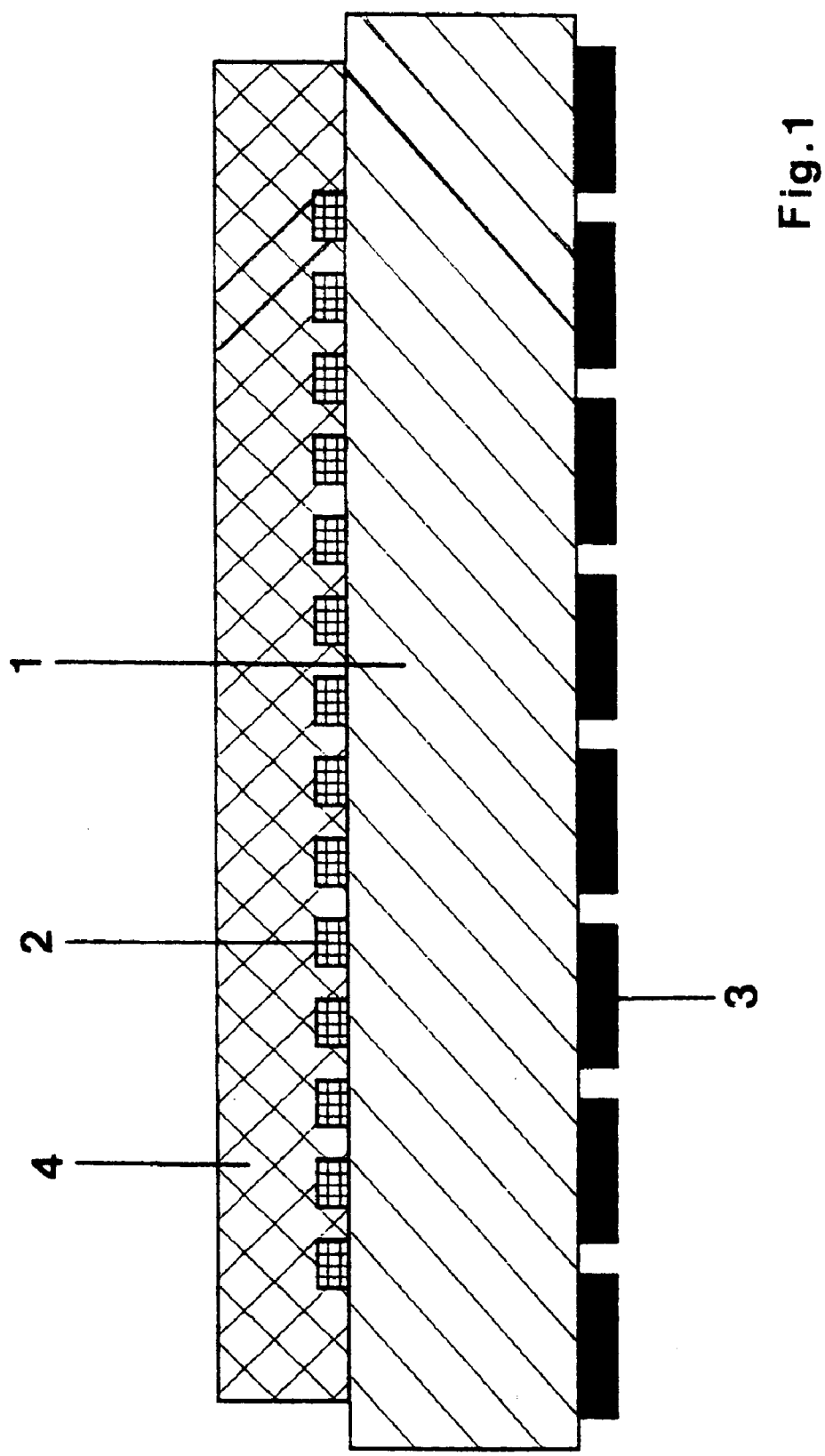
FIG. 1 is a sectional side view of a simple soot sensor on a carrier according to a first embodiment of the invention.

FIG. 1 shows a soot sensor in cross section with a carrier 1 of $Al_2O_3$ ceramic. On one side of the carrier 1 a meander-shaped temperature probe 2 is arranged, here a platinum resistance element made by thin film technology. This temperature probe 2 is covered by an open-pored ceramic molded element 4 of $Al_2O_3$. On the other side of the carrier 1 a meander-shaped heating element 3 is arranged.

Figure 2:
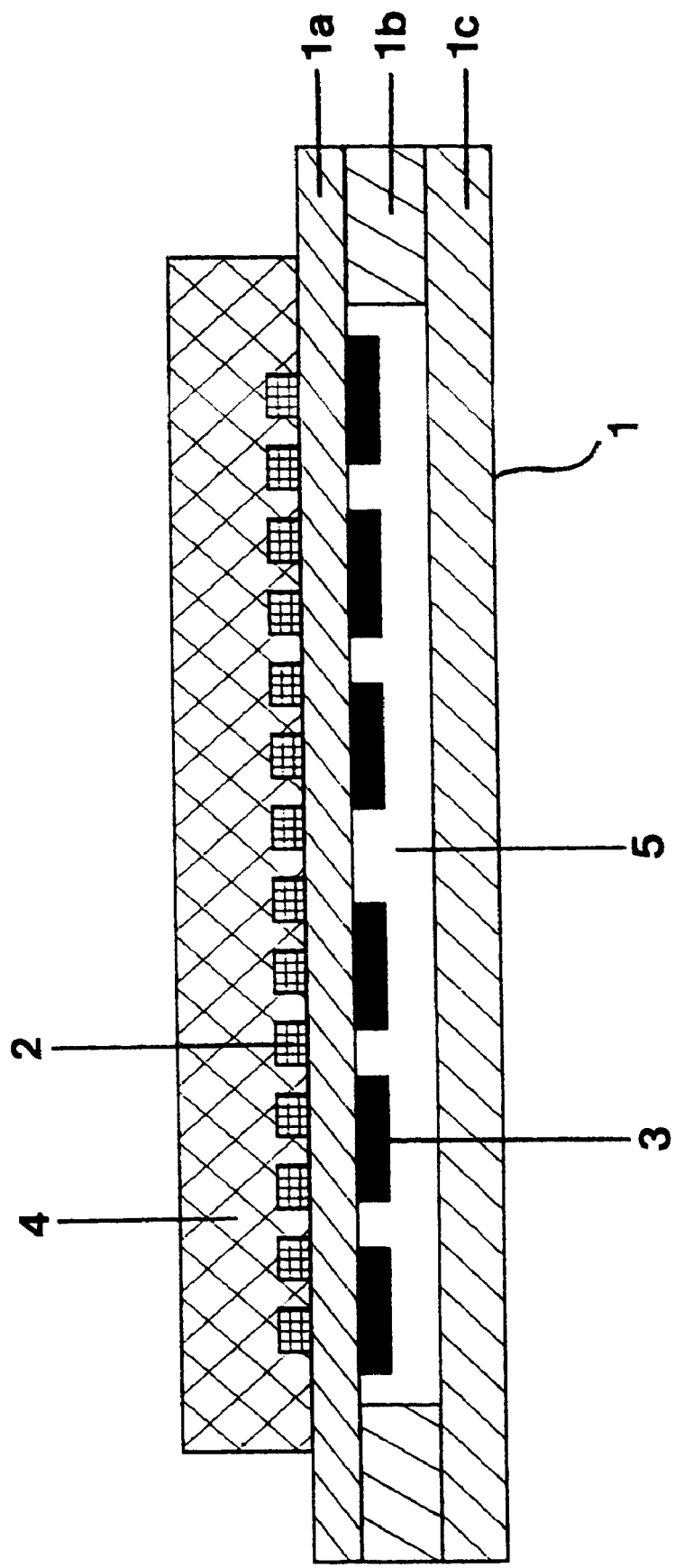
FIG. 2 is a sectional side view of a soot sensor with a heating element in a soot-free gas space according to a second embodiment.

FIG. 2 illustrates a soot sensor in cross section with a carrier 1 which is made of the gas-impermeable, ceramic sheets 1a; 1b; 1c, using lamination technology. On one side of the carrier 1 a meander-shaped temperature probe 2 is arranged, covered by an open-pored ceramic molded element 4. The carrier 1 forms a soot-free gas space 5 in which a protected, meander-shaped heating element 3 is arranged.

Figure 3:
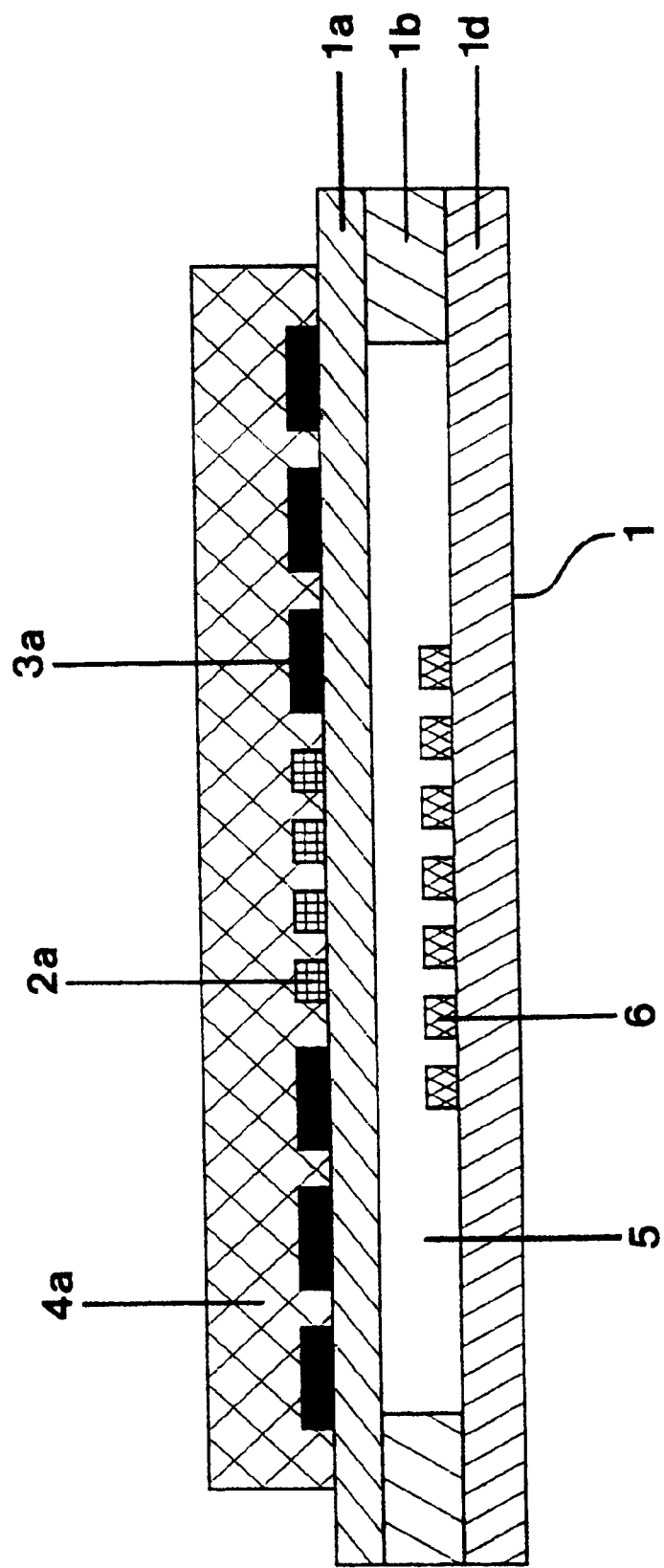
FIG. 3 is a sectional side view of a soot sensor with an additional temperature probe in a soot-free gas space according to a third embodiment.

FIG. 3 shows a soot sensor in cross section with a carrier 1 of $Al_2O_3$, which is made of the gas-impermeable, ceramic sheets 1a; 1b and the gas-permeable, ceramic sheet 1d, using lamination technology. On one side of the carrier 1 a meander-shaped temperature probe 2a is arranged, surrounded by a meander-shaped heating element 3a. The individual paths of the temperature probe 2a and the heating element 3a are covered by an electrically insulating, soot-impermeable, thin layer of $Al_2O_3$ (not represented here), which in turn is covered by the open-pored ceramic molded element 4a. The pore surfaces of the molded element 4a are coated with a catalytically active material, here platinum. The carrier 1 forms a soot-free gas space 5, in which an additional temperature probe 6 is arranged for independent measurement of the exhaust gas temperature. The gas permeable, ceramic sheet 1d makes possible an entry of the exhaust gas without soot particles into the gas space 5 and thereby contributes to increasing the response rate of the additional temperature probe 6.

Figure 4:
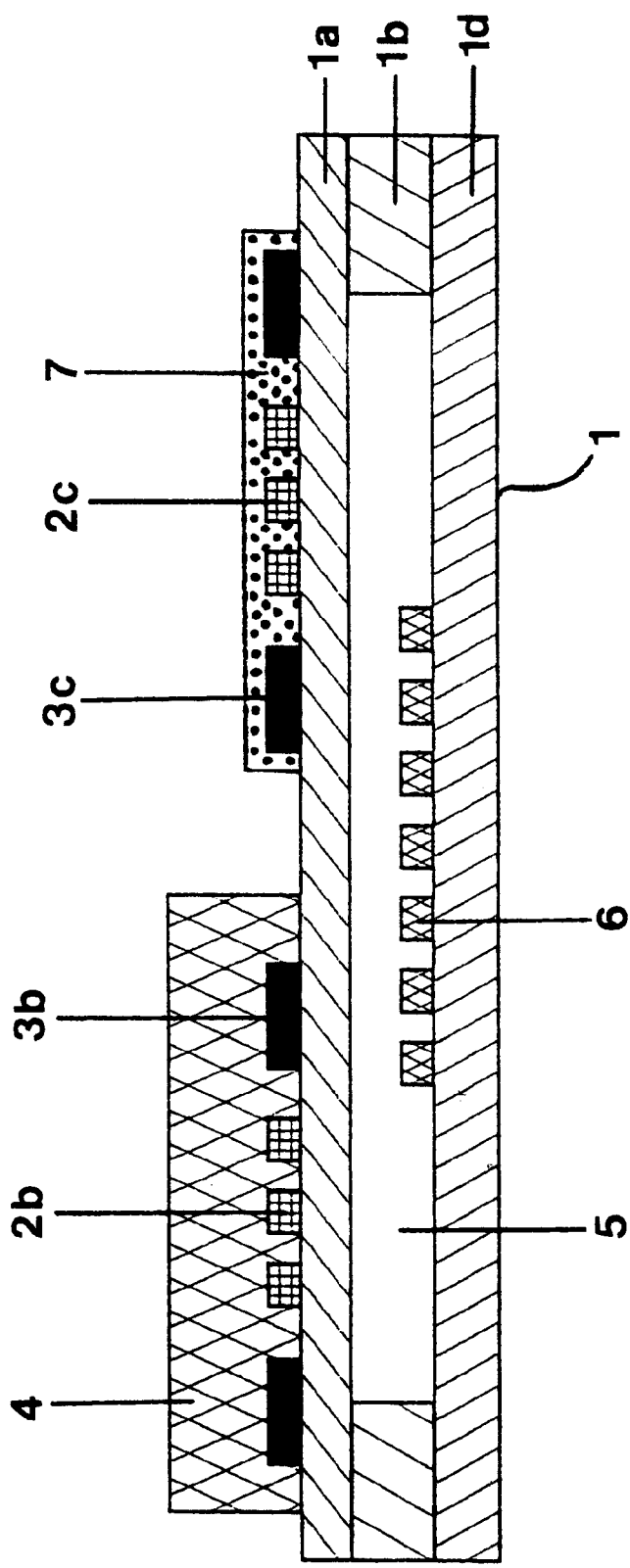
FIG. 4 is a sectional side view of a soot sensor with an additional temperature probe and an additional heating element in the exhaust gas stream, as well as an additional temperature probe in a soot-free gas space according to a fourth embodiment.

FIG. 4 depicts a soot sensor in cross section with a carrier 1, which is made of the gas-impermeable, ceramic sheets 1a; 1b and the gas-permeable, ceramic sheet 1d using lamination technology. On one side of the carrier 1 a meander-shaped temperature probe 2b is arranged, surrounded by an annular heating element 3b. The temperature probe 2b and the heating element 3b are covered by an open-pored ceramic molded element 4. On this side of the carrier 1 a further meander-shaped temperature probe 2c is arranged, surrounded by an annular heating element 3c. The temperature probe 2c and heating element 3c are coated with a soot-impermeable protective layer 7. The parallel operation of temperature probes 2b; 2c and heating elements 3b; 3c makes possible a difference measurement. Here, the heating elements 3b; 3c are operated in the same manner by a control unit, and when the ignition temperature of the soot is reached, the measured signal of temperature probe 2c is subtracted from that of temperature probe 2b. A measured result emerges, which unambiguously and with great accuracy can be attributed to the development of heat, which arises due to the combustion of the soot. The carrier 1 forms a soot-free gas space 5, in which an additional temperature probe 6 is arranged for independent measurement of the exhaust gas temperature. The gas-permeable, ceramic sheet 1d makes possible an entry of the exhaust gas without soot particles into the gas space 5 and thereby contributes to increasing the response rate of the additional temperature probe 6.

Figure 5:
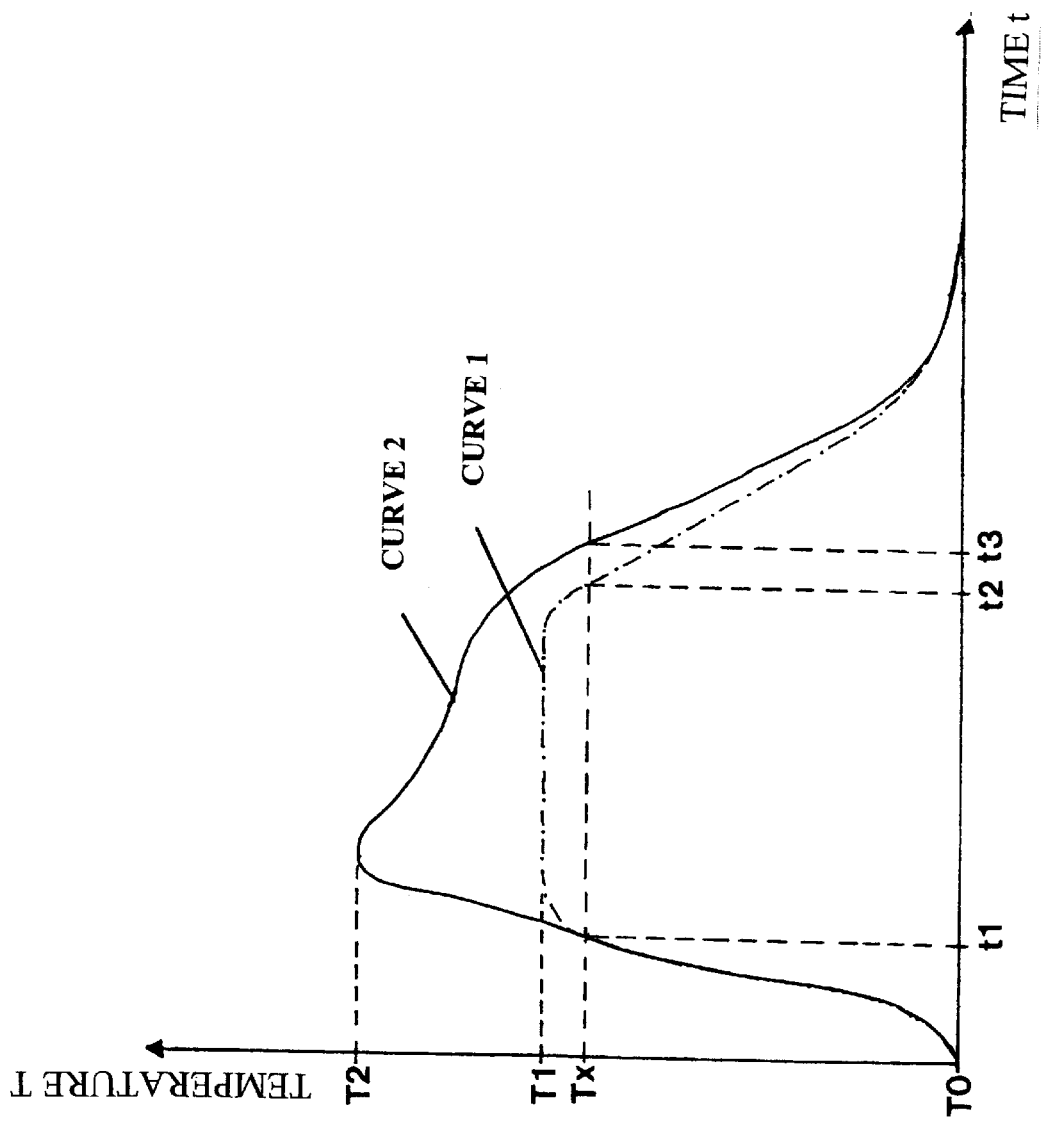
FIG. 5 is a graphical diagram for measuring the temperature progression of the molded element of FIG. 1 with and without soot.

FIG. 5 illustrates the temperature progression of a molded element, as shown in FIG. 1, which is heated with a heating element proceeding from a temperature T0 in the exhaust gas conduit of a diesel motor vehicle. This temperature T0 can generally be synonymous with the cold start temperature of the motor or with any desired temperature of the exhaust gas stream. Here, the case is considered in which the molded element is heated during the pre-glow process upon cold start of the motor vehicle to the ignition temperature of the soot. A rapid change in the ambient temperature, which would influence the measurement and would therefore have to be recorded and compensated for, is not to be feared at this time (thus before starting the motor). Consequently, an additional measurement of the ambient temperature is not necessary in this case. Curve 1 illustrates the temperature curve of the molded element without soot loading, recorded with a temperature probe, wherein the heat output of the heating element is held constant over a time t. This curve 1 represents a reference curve, which should always be stored in the control unit of the motor vehicle for the evaluation of the curves with soot.

Curve 2 shows the temperature progression of the molded element with soot loading, recorded with the same temperature probe, wherein the heat output of the heating element is kept constant over a time t. Due to the combustion of the soot, higher temperatures are reached in curve 2 than in curve 1. The difference between the maximum temperatures T1 and T2 of curves 1 and 2 can be used to calculate the amount of soot on the molded element, and this value can be brought into relationship with the amount of soot found on an after-connected soot filter, by a correlation formula stored in the control unit, which was determined in advance specially for the measurement structure used and the materials used for the soot filter and the soot sensor. Of course, for an average technician, instead of such a mathematical evaluation of the curves as to their slope, an integral formation or an evaluation over time is also possible. Thus, for example, for curve 1 a time t2–t1 can be determined, and for curve 2 a time t3–t1 can be determined, which indicates how long the soot sensor has a temperature T above a temperature Tx. If a temperature Tx somewhat below T1 is selected, then the differences between time t2–t1 and time t3–t1 are shown most clearly. A difference between the times (t2–t1) and (t3–t1), which indicates subsequent cooling due to the combustion of soot on the soot sensor, represented in curve 2, can be correlated with the amount of soot combusted, since a value t2–t1 for a temperature Tx of a non-loaded sensor is stored in a control unit for purposes of comparison, and at a temperature Tx on the soot sensor the time t3–t1 is determined, and the difference is formed with the aid of the stored value.

Figure 6:
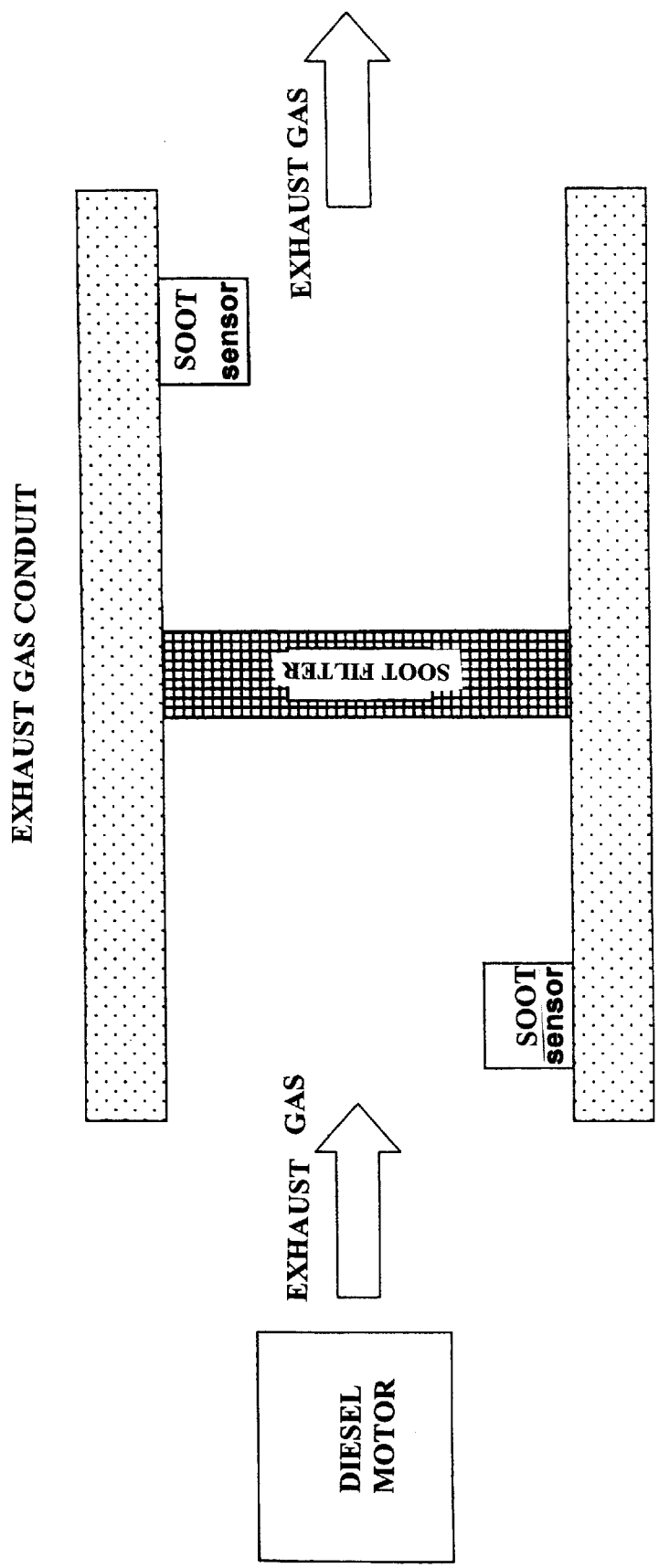
FIG. 6 is a schematic representation illustrating use of the present invention with two soot sensors in an exhaust gas conduit.

FIG. 6 shows a schematic representation with two soot sensors in an exhaust gas conduit. The soot-containing exhaust gas ejected from a diesel engine is introduced into the exhaust gas conduit. A portion of the exhaust gas stream flows by a soot sensor arranged upstream of a soot filter in the flow direction and flows through its open-pored molded element. Here, a small portion of the soot found in the exhaust gas is separated off on the openpored molded element. With this soot sensor arranged upstream of the soot filter, the loading of the soot filter can be determined in the manner described above, and the cleaning of the soot filter can be occasioned when needed. The exhaust gas comes upon the soot filter after the first soot sensor through which it must flow. A second soot sensor is situated after the soot filter in the flow direction in the exhaust gas conduit, with which the gas purified by the soot filter comes into contact. This second soot sensor is used to detect leaks in the soot filter.

Figure 7:
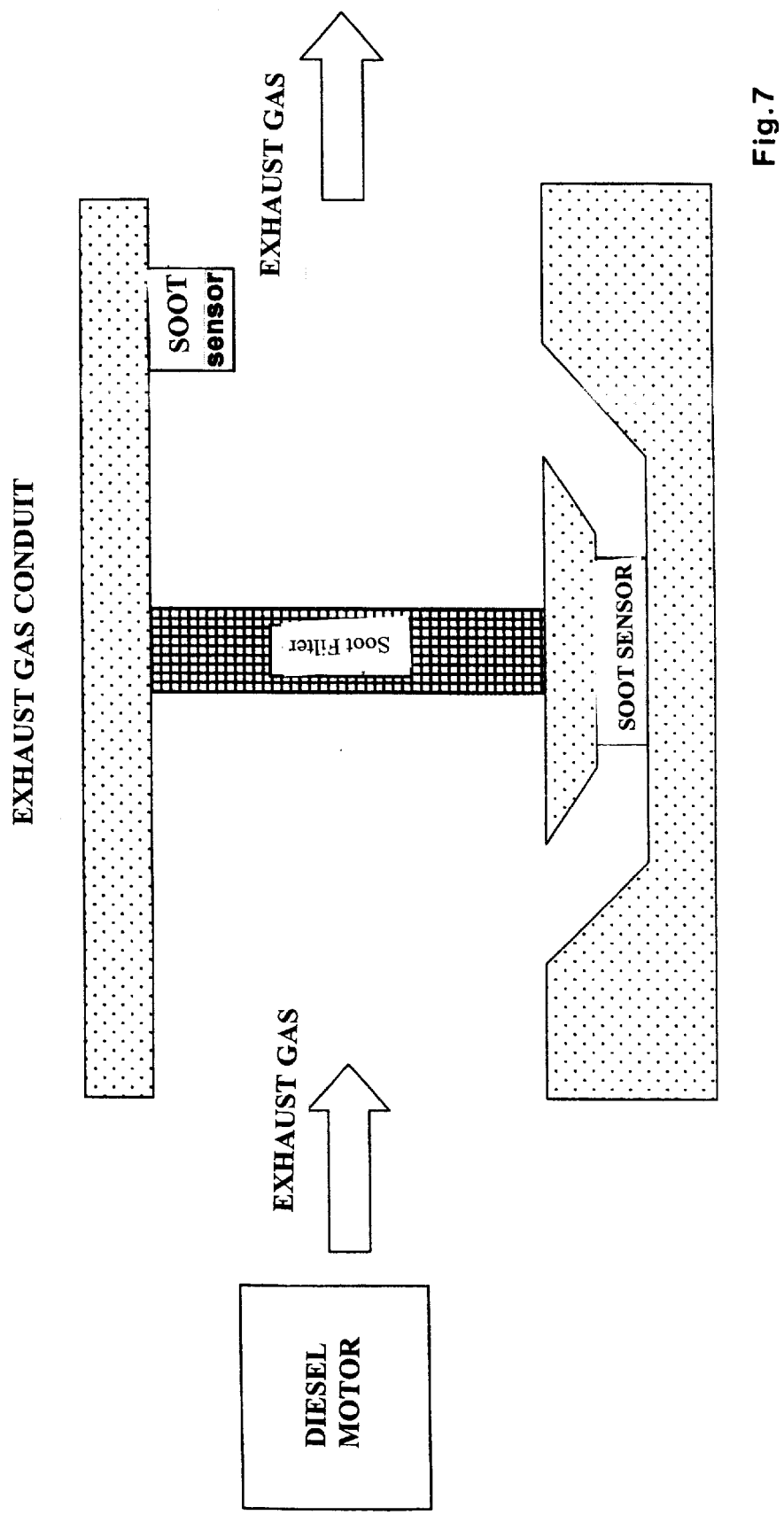
FIG. 7 is a schematic representation illustrating another system for use of the invention with a soot sensor in a bypass to the exhaust gas conduit and a second soot sensor in an exhaust gas conduit.

FIG. 7 gives a schematic representation with a soot sensor in an exhaust gas bypass to the soot filter and a second soot sensor after the soot sensor in the flow direction in the exhaust gas conduit. The function of the soot sensor in the exhaust gas bypass is identical with that of the first soot sensor in the flow direction from FIG. 6.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A measuring arrangement comprising a soot filter for use in flowing, soot particle-bearing gases, and at least one soot sensor associated with the soot filter, the soot sensor comprising at least one molded element (4) which is open-pored at least in a flow direction of the gases, at least one electric heating element (3; 3a; 3b; 3c) for heating the molded element, and at least one temperature probe (2; 2a; 2b; 2c) for measuring a temperature of the molded element due to soot particle combustion, wherein the molded element (4) is adapted and arranged for flow through of the gases such that only a representative portion of soot particles is removed from the gases.

2. The measuring arrangement according to claim 1, wherein the soot sensor is arranged upstream of the soot filter.

3. The measuring arrangement according to claim 1, wherein the soot sensor is arranged in an exhaust gas bypass to the soot filter.

4. The measuring arrangement according to claim 1, wherein the soot sensor is arranged downstream of the soot filter.

5. The measuring arrangement according to claim 1, wherein a first soot sensor is arranged upstream of the soot filter and a second soot sensor is arranged downstream of the soot filter.

6. The measuring arrangement according to claim 1, wherein the molded element (4), which is open-pored at least in the flow direction, is formed of a ceramic with a honeycomb construction.

7. The measuring arrangement according to claim 1, wherein the molded element (4) is at least partially coated with a catalytically active material.

8. The measuring arrangement according to claim 1, wherein the electric heating element (3; 3a; 3b; 3c) and the temperature probe (2; 2a; 2b; 2c) are arranged directly on or in the molded element (4).

9. The measuring arrangement according to claim 1, wherein the electric heating element (3; 3a; 3b; 3c), the temperature probe (2; 2a; 2b; 2c) and the molded element (4) are arranged on a carrier (1; 1a; 1b; 1c; 1d).

10. The measuring arrangement according to claim 1, which is mounted in the exhaust gas conduit of a motor vehicle for verifying operability of the soot filter.

11. A method for monitoring the operability of a soot filter arranged in an exhaust gas conduit, comprising flowing at least a component stream of a soot particle-bearing, exhaust gas stream through at least one molded element which is open-pored at least in a flow direction of the gas stream, measuring a temperature of the at least one molded element with at least one temperature probe, wherein a portion of the soot particles remains adhered to the molded element (4), heating up the molded element (4) is at defined time intervals by an electrical heating element (3; 3a; 3b) to an ignition temperature of the soot, and using a development of heat occurring upon combustion of soot particles as a direct measure for operability of the soot filter.

12. The method according to claim 11, wherein the time intervals are selected as fixed.

13. The method according to claim 11, wherein the time intervals are selected on a basis of an evaluation of operating data.

14. The method according to claim 11, further comprising, after reaching the ignition temperature of the soot on the molded element (4), operating the electric heating element (3; 3a; 3b) with a constant heat output, measuring the development of heat occurring due to combustion of soot particles with the temperature probe (2; 2a; 2b), evaluating a temperature rise as a direct measure for a combusted amount of soot particles on the molded element (4), and determining therefrom the operability of the soot filter.

15. The method according to claim 11, further comprising, after reaching an ignition temperature of the soot on the molded element (4), maintaining a temperature of the molded element (4) substantially isothermal by withdrawing a heat output of the electric heating element (3; 3a; 3b), evaluating the heat output as a direct measure for a combusted amount of soot particles on the molded element (4), and determining therefrom the operability of the soot filter.

16. The method according to claim 11, wherein the molded element (4) is arranged upstream of the soot filter in the flow direction, and after reaching the ignition temperature of the soot upon occurrence of a development of heat on the molded element (4), a loading of the soot filter with soot particles is ascertained.

17. The method according to claim 11, wherein the molded element (4) is arranged downstream of the soot filter in the flow direction, and after reaching the ignition temperature of the soot upon occurrence of a development of heat on the molded element (4), a leak of the soot filters is determined, and a warning signal is emitted, which indicates a defect in the soot filter, if the development of heat exceeds a predetermined threshold value.

18. The method according to claim 11, wherein a first molded element (4) is arranged upstream of the soot filter in the flow direction and a second molded element (4) is arranged downstream of the soot filter in the flow direction, and, after reaching the ignition temperature of the soot upon occurrence of a heat development on the first molded element (4), a loading of the soot filter with soot particles is ascertained, and, after reaching the ignition temperature upon occurrence of a heat development on the second molded element (4), a leak of the soot filter is determined, and a warning signal is emitted, which indicates a defect of the soot filter, if the development of heat exceeds a predetermined threshold value.

19. The method according to claim 11, wherein the molded element (4) is arranged in an exhaust gas bypass to the soot filter, and, after reaching the ignition temperature of the soot upon occurrence of a development of heat on the molded element (4), a loading of the soot filter with soot particles is ascertained.

* * * * *